QUINOLIN-2-(1H)-ONES

[75] Inventors: Karl-August Ackermann, Ober-Ramstadt; Rudlof Gottschlich, Reinheim; Günter Hölzemann, Seeheim; Joachim Leibrock, Griesheim; Wilfried Rautenberg, Reinheim; Christoph Seyfried, Seeheim, all of Germany

[73] Assignee: Merck Patent Gesellschaft Mit Beschrankter Haftung, Germany

[21] Appl. No.: 09/101,837

[22] PCT Filed: Jan. 10, 1997

[86] PCT No.: PCT/EP97/00084

§ 371 Date: Jul. 17, 1998

§ 102(e) Date: Jul. 17, 1998

[87] PCT Pub. No.: WO97/26244

PCT Pub. Date: Jul. 24, 1997

[30] Foreign Application Priority Data

Jan. 19, 1996 [DE] Germany ............ 196 01 782

[51] Int. Cl.[7] ............ A61K 31/47; C07D 215/22; C07D 217/04

[52] U.S. Cl. ............ 514/307; 514/312; 546/144; 546/148; 546/155

[58] Field of Search ............ 546/148, 144, 546/155; 514/307, 312

[56] References Cited

U.S. PATENT DOCUMENTS 5,268,378 12/1993 Baker et al. ............ 514/312
5,348,962 9/1994 Kulagowski ............ 514/312
5,614,532 3/1997 Carling et al. ............ 514/312

FOREIGN PATENT DOCUMENTS 459561 12/1991 European Pat. Off. .
481676 4/1992 European Pat. Off. .
685466 12/1995 European Pat. Off. .
9311115 6/1993 WIPO .

OTHER PUBLICATIONS

English abstract for EP 685466.

Primary Examiner—Evelyn Mei Huang
Attorney, Agent, or Firm—Millen, White, Zelano & Branigan, P.C.

[57] ABSTRACT

The invention relates to quinoline-2-(1H)-one derivatives of the general formula I

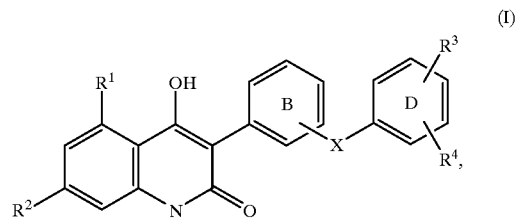

in which $R^1$, $R^2$ and $R^3$ are in each case independently of one another H, Hal, A or OA; $R^4$ is H, $-(CH_2)_m-NR^6R^7$; $R^5$ is H, $-(CH_2)_n-NR^6R^7$; $R^6$ is H, A or, together with $R^7$, $-(CH_2)_4-$ or $-(CH_2)_5-$; $R^7$ is H, A or $-(CH_2)_m-$ with a bond to the same ring or adjacent ring B or D or, together with $R^6$, $-(CH_2)_4-$ or $-(CH_2)_5-$; X is $-CHR^5-$, $-NR^5-$, $-O-$, $-S-$; A is alkyl having 1–6 C atoms; Hal is F, Cl, Br or I; m is 1–3 and n is 0–3, where at least one of the two radicals $R^4$ or $R^5$ has the meaning $-(CH_2)_m-NR^6R^7$ or $-(CH_2)_n-NR^6R^7$, their enantiomers, stereoisomers, salts and solvates. Such compounds are useful for the treatment of neurodegenerative diseases.

14 Claims, No Drawings

QUINOLIN-2-(1H)-ONES

This application is the national phase of PCT/EP97/00084, filed on Jan. 10, 1997

The invention relates to quinolin-2-(1H)-one derivatives of the formula I

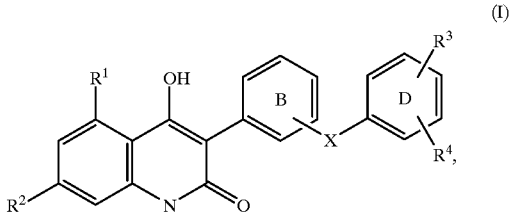

in which $R^1$, $R^2$ and $R^3$ are in each case independently of one another H, Hal, A or OA, $R^4$ is H, —$(CH_2)_m$—$NR^6R^7$, $R^5$ is H, —$(CH_2)_n$—$NR^6R^7$, $R^6$ is H, A or, together with $R^7$, —$(CH_2)_4$— or —$(CH_2)_5$—, $R^7$ is H, A or —$(CH_2)_m$— with a bond to the same ring or adjacent ring B or D or, together with $R^6$, —$(CH_2)_4$— or —$(CH_2)_5$—, X is —$CHR^5$—, —$NR^5$—, —O—, —S—, A is alkyl having 1–6 C atoms, Hal is F, Cl, Br or I, m is 1–3 and n is 0–3, where, however, at least one of the two radicals $R^4$ or $R^5$ has the meaning —$(CH_2)_m$—$NR^6R^7$ or —$(CH_2)_n$—$NR^6R^7$, and their salts and solvates.

This invention also relates to the use of these compounds and their physiologically acceptable salts for the treatment of neurodegenerative changes in CNS functions.

The Patent Applications WO 93/11115 A1 and EP 0 481 676 A1 disclose quinolin-2-(1H)-one derivatives which act as antagonists of glutamate receptors, in particular of NMDA receptors. On account of these properties, the compounds are described as suitable for the treatment of acute neurodegenerative disorders which are caused by stroke or hypoglycaemia, cerebral palsy, transient cerebral ischaemic attacks, cerebral ischaemias during surgical heart-lung interventions or cardiac arrests, perinatal asphyxia, epilepsy, Huntington's chorea, Alzheimer's disease, amyotrophic lateral sclerosis, Parkinson's disease, atrophy of the cerebellum, anoxias due to drowning, bone marrow and head injuries, intoxification due to exogenous and endogenous NMDA receptor agonists or neurotoxins, including those in the environment.

Additionally, appropriate compounds should also be suitable for the prevention of neurodegenerative disorders or, on account of their NMDA receptor-antagonistic properties, employable as antispasmodics, analgesics, antiemetics, or for the prevention or reduction of the dependence potential of narcotics.

It was not known until now and was therefore surprising that the quinolin-2-(1H)-ones, substituted in the in [sic] 3-position by various phenyl groups, of the present invention exhibit this activity for the indications mentioned. This applies in particular to the use of these medicaments in liquid form; to be precise particularly if they are administered in an infusion solution. This type of administration is necessary in the case of unconsciousness of the patient to be treated.

It was therefore an object of the present invention to provide compounds having improved neuroprotective action.

It was furthermore an object of this invention to make available processes by means of which the appropriate compounds can be prepared in the highest possible yields and high purities.

This object is achieved by the present invention.

It has now been found that compounds of the formula I, in which the radicals $R^1$ to $R^7$, A, Hal, X, m and n have the given meanings, and their physiologically acceptable salts have useful pharmacological properties. In particular, these compounds are selective antagonists of N-methyl-D-aspartate receptors (NMDA receptor antagonists). The compounds according to the invention have proved in particular to be selective ligands of the strychnine-insensitive glycine receptor, which modulates the NMDA receptor. They are therefore suitable for the treatment of neurodegenerative disorders, including cerebrovascular diseases. They are particularly highly suitable for the treatment of acute neurodegenerative disorders which are caused by stroke or hypoglycaemia, cerebral palsy, transient cerebral ischaemic attacks, cerebral ischaemias during surgical heart-lung interventions or cardiac arrest, perinatal asphyxia, anoxias due to drowning, bone marrow and head injuries, intoxification by exogenous and endogenous NMDA receptor agonists or by neurotoxins, but also due to epileptic attacks or due to Huntington's chorea.

Experiments have shown that the compounds according to the invention are particularly effective in the case of an infarct. They can therefore be administered to the patient, for example in the unconscious state, in the form of infusion solutions.

The compounds according to the invention, however, are also suitable for the prevention of appropriate neurodegenerative disorders, such as occur in Alzheimer's disease, Parkinson's disease, atrophy of the cerebellum, an amyotrophic lateral sclerosis or intoxifications due to environmental toxins. They are furthermore suitable for the treatment of psychoses caused by excessively high amino acid levels.

On account of their NMDA receptor-antagonistic properties, the appropriate compounds according to the invention can be of value as antispasmodics, analgesics, in particular in the case of migraine, antidepressants or anxiolytics, antiemetics or for the prevention or reduction of the dependence potential of narcotics.

All in all, this means that the compounds according to the invention can be effectively employed in all indications which are associated with an unusual increase in the extracellular glutamate concentration of the brain, and in which both the activity of the NMDA and of the AMPA receptors is raised. Their use is therefore particularly preferred in situations in which an immediate effect on the NMDA receptors is desirable, for example in disorders of the cerebral functions as a result of vascular damage or occlusions or as a result of an oxygen deficiency associated with an energy deficient in the brain. The possibility exists in such cases of administering the compounds according to the invention by injection and/or infusion, which is particularly advantageous in this situation. Since in these cases therapeutically only very little time is available, for the patients the prospects for a possible and complete cure are all the better the more rapidly the active compound reaches the site of action.

A test for the glycine binding site of the NMDA receptor according to the method of M. B. Baron et al., is described in Eur. J. Pharmacol. (1991) 206 149–154. The in vitro amino acid release can be detected according to the method of D. Lobner and P. Lipton (Neurosci. Lett. (1990) 117, 169–174). The action against Parkinson's disease, i.e. the potentiation of the L-Dopa-induced contralateral rotation in hemiparkinson rats, can be detected according to the method of U. Ungerstedt and G. W. Arbuthnott, Brain Res. (1970) 24, 485.

The actions mentioned can additionally be detected or checked by the methods such as are given in the following literature references:

J. W. McDonald, F. S. Silverstein and M. v. Johnston, Eur. J. Pharmacol. (1987) 140, 359; R. Gill, A. C. Foster and G. N. Woodruff, J. Neurosci. (1987) 7, 3343, S. M. Rothmann, J. H. Thurston, R. E. Hauhart, G. D. Clark and J. S. Solomon, Neurosci. (1987) 21, 73 or M. P. Goldbert, P.—C. Pham and D. W. Choi, Neurosci. Lett. (1987) 80, 11.

The compounds can therefore be used as pharmaceutical active compounds in human and veterinary medicine. They are furthermore suitable as intermediates for the preparation of other compounds having useful properties.

The invention accordingly relates to compounds of the formula I, their salts and their use, and to suitable processes for the preparation of the compounds according to the invention.

In the formula I, A is alkyl having 1, 2, 3, 4, 5 or 6 C atoms, in particular methyl or ethyl, but also propyl, isopropyl, butyl, isobutyl, sec-butyl or tert-butyl. The group OA is accordingly preferably methoxy, ethoxy, propoxy, isopropoxy, butoxy, isobutoxy, sec-butoxy or tert-butoxy, the group —NA— is preferably N-methyl- and the group —NHA is NH-methyl.

$R^1$ is preferably H, Hal or A. $R^1$ is particularly preferably H or Hal.

$R^2$ is preferably a halogen or an alkoxy group OA. It is particularly preferably F or Cl.

$R^3$ is preferably H or A.

$R^4$ is preferably H or —(CH$_2$)$_m$—NR$^6$R$^7$ where R$^6$ is H, A or, together with R$^7$, —(CH$_2$)$_4$— or —(CH$_2$)$_5$—, and where R$^7$ is H, A or —(CH$_2$)$_m$— with a bond to the same or adjacent ring, or together with R$^6$ is —(CH$_2$)$_4$— or —(CH$_2$)$_5$—.

$R^5$ is preferably H or —(CH$_2$)$_n$—NR$^6$R$^7$ where R$^6$ is H, A or, together with R$^7$, also —(CH$_2$)$_4$— or —(CH$_2$)$_5$—, and where R$^7$ is H, A or —(CH$_2$)$_m$— with a bond to the same or adjacent ring, or together with R$^6$ is —(CH$_2$)$_4$— or —(CH$_2$)$_5$—.

X is preferably —CHR$^5$—, O or —NR$^5$—, where R$^5$ is preferably H if R$_4$ is —(CH$_2$)$_m$—NR$^6$R$^7$.

The invention accordingly relates in particular to those compounds of the formula I in which at least one of the radicals mentioned has one of the preferred meanings given above. Some preferred groups of compounds can also be expressed by the formulae below, which correspond to the formula I and in which the radicals not described in greater detail have the meanings given under formula I, but in which in Ia $R^1$ is H or Hal, $R^2$ is Hal, X is —CHR$^5$— where $R^5$ is —(CH$_2$)$_m$—NR$^6$R$^7$, in which $R^6$ is methyl and $R^7$ is —(CH$_2$)$_m$— with a bond to the ring B in Ib $R^1$ is H or Hal, $R^2$ is Hal, X is —CHR$^5$— where $R^5$ is —(CH$_2$)$_m$—NR$^6$R$^7$, in which $R^6$ is methyl and $R^7$ is —(CH$_2$)$_m$— with a bond to the ring D in Ic $R^1$ is H or Hal, $R^2$ is Hal, X is —CHR$^5$— where $R^5$ is H, $R^4$ is —(CH$_2$)$_m$—NR$^6$R$^7$, in which $R^6$ is methyl and $R^7$ is —(CH$_2$)$_m$— with a bond to the ring B in Id $R^1$ is H or Hal, $R^2$ is Hal, X is —CHR$^5$— where $R^5$ is H, $R^4$ is —(CH$_2$)$_m$—NR$^6$R$^7$, in which $R^6$ is methyl and $R^7$ is —(CH$_2$)$_m$— with a bond to the ring D in Ie $R^1$ is H or Hal, $R^2$ is Hal, X is —CHR$^5$— where $R^5$ is H, $R^4$ is —(CH$_2$)$_m$—NR$^6$R$^7$, in which $R^6$ is methyl and $R^7$ is —(CH$_2$)$_m$— with a bond to the ring D in If $R^1$ is H or Hal, $R^2$ is Hal, X is —CHR$^5$— where $R^5$ is H, $R^4$ is —(CH$_2$)$_m$—NR$^6$R$^7$, in which $R^6$ and $R^7$ together are —(CH$_2$)$_m$— and form a heterocycle jointly with the nitrogen in Ig X is —CHR$^5$— where $R^5$ is —(CH$_2$)$_m$—NR$^6$R$^7$, in which $R^6$ and $R^7$ together are —(CH$_2$)$_m$— and form a heterocycle jointly with the nitrogen.

Compounds of the formulae 2a to 2d are furthermore preferred which correspond to the formulae I and Ic to If, but in which X is O.

For the use of the compounds of the formula I as pharmaceutically active substances, both the compounds per se and their physiologically tolerable salts can be employed. Other salts can be used for the release of compounds of the formula I according to the invention. However, they can, for their part, also be converted into physiologically tolerable salts or used as intermediates for the preparation of other active compounds. Suitable salts of the compounds of formula I which can be employed pharmaceutically are alkali metal salts, such as lithium, sodium or potassium salts, alkaline earth metal salts, such as calcium or magnesium salts, or alternatively salts formed with quaternary ammonium compounds. In the context of the invention, compounds of the formula I, however, can also be present as salts of physiologically tolerable acids. In particular, they can be present as salts of hydrochloric acid, methanesulfonic acid, fumaric acid, maleic acid, succinic acid, acetic acid, citric acid, tartaric acid, malic acid, formic acid or phosphoric acid.

Compounds of the formula I according to the invention can have centres of asymmetry and accordingly occur in several enantiomeric or diastereomeric forms. On account of one or more chiral centres, they can therefore be present in racemic or in optically active form. All these forms and their mixtures are included in the formula I. Since the pharmaceutical activity of the individual forms can differ, it may be desirable to use the pure isomers or enantiomers. In these specific cases the final product can be resolved into enantiomerically pure compounds by chemical measures known to the person skilled in the art, but in isolated cases also by mechanical measures. Preferably, diastereomers are formed from the racemic mixture by reaction with an optically active resolving agent. Suitable resolving agents are, for example, optically active acids, such as the D- and L-forms of tartaric acid, diacetyltartaric acid, dibenzoyltartaric acid, mandelic acid, malic acid, lactic acid or the various optically active camphorsulfonic acids such as β-camphorsulfonic acid. Resolution of enantiomers with the aid of a column packed with an optically active resolving agent (e.g. dinitrobenzoylphenylglycine) is also advantageous. Suitable eluents for this purpose are, for example, a mixture of hexane/isopropanol/acetonitrile, e.g. in the ratio 82:15:3.

Under particular conditions, however, it is also possible even during the synthesis to employ appropriate enantiomerically pure intermediates.

Accordingly, all enantiomeric or diastereomeric forms of the intermediates described in the following are likewise additionally included in the following general formulae.

The invention furthermore also relates to the preparation of quinolin-2-(1H)-one derivatives of the formula I according to claim 1, and their salts. According to one such process for the preparation, compounds of the formula I can be prepared by a cyclization reaction by [lacuna] a suitable compound of the formula II

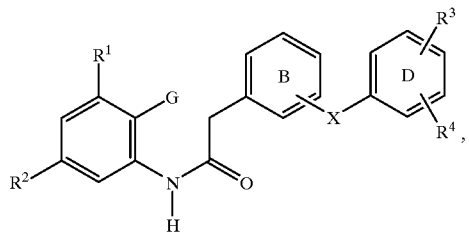

(II)

in which $R^1$, $R^2{}_1$, $R^3$ and $R^4$ and X have the meanings given, and G is a cyano group or a reactive carboxylate group [lacuna]. A reactive carboxylate group can be an ester group, preferably an alkyl ester group having one to four C atoms in the alkyl moiety, or a mixed anhydride, e.g. an anhydride of an acid having one to four C atoms; an acid halide group, such as, for example, an acid chloride group, an ortho ester group or a primary, secondary or tertiary amide. Preferred reactive carboxylate groups are methoxycarbonyl or ethoxycarbonyl.

The cyclization can be carried out by methods known per se under mild conditions in the presence of a base, such as, for example, sodium hydride or potassium hexamethyldisilazide (J. Heterocycl. Chem. (1975) 12, 351). Working up is carried out under mild, weakly acidic conditions.

The cyclization of a suitable compound in which G is a cyano group leads to a quinolin-2-(1H)-one derivative of the formula I which, however, is substituted in the 4-position by an amino group. This amino group can be converted into the desired hydroxyl group by known methods if further amino groups contained in the compound are inaccessible in the reaction due to protective groups.

According to the general formula, up to two—identical or different—protected amino groups can be present in the molecule of the starting substance. If the protective groups present are different from one another, in many cases they can be removed selectively.

The expression "amino protective group" is generally known and relates to groups which are suitable for protecting an amino group from chemical reactions, but which are easily removable after the desired chemical reaction has been carried out at another position in the molecule. Typical of such groups are, in particular, unsubstituted or substituted acyl, aryl (e.g. dinitrophenyl (DNP), aralkoxymethyl (e.g. benzoxymethyl (BOM)) or aralkyl groups (e.g. benzyl, 4-nitrobenzyl, triphenylmethyl). As the amino protective groups are removed after the desired reaction (or reaction sequence), their nature and size is otherwise uncritical; however those having 1–20, in particular 1–8, C atoms are preferred.

The expression "acyl group" is to be interpreted in the widest sense in connection with the present process. It includes acyl groups derived from aliphatic, araliphatic, aromatic or heterocyclic carboxylic acids or sulfonic acids, and in particular alkoxycarbonyl, aryloxycarbonyl and especially aralkoxycarbonyl groups. Examples of acyl groups of this type are alkanoyl such as acetyl, propionyl, butyryl; aralkanoyl such as phenacetyl; aroyl such as benzoyl or tolyl; aryloxyalkanoyl such as phenoxyacetyl; alkoxycarbonyl such as methoxycarbonyl, ethoxycarbonyl; 2,2,2-trichloroethoxycarbonyl, isopropoxycarbonyl, tert-butoxycarbonyl (BOC), 2-iodoethoxycarbonyl; aralkyloxycarbonyl such as benzoyloxycarbonyl [sic] (CBZ), 4-methoxybenzyloxycarbonyl, 9-fluorenylmethoxycarbonyl (FMOC). Preferred amino protective groups are BOC, DNP and BOM, furthermore CBZ, benzyl and acetyl.

Compounds of the formula II can be prepared by methods known per se from compounds of the formula III

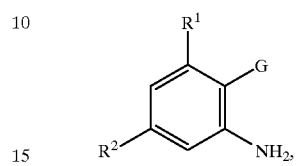

(III)

in which G has the meaning given above, and IV

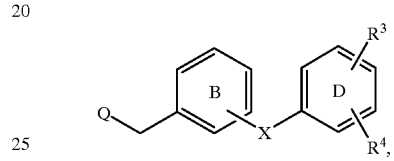

(IV)

in which $R^3$, $R^4$ and X have the meaning given above and Q is a reactive carboxylate group as given above. Preferably, Q is an acid halide group, to be precise preferably an acid chloride group. A compound of the formula IV in which Q is an acid chloride group can be prepared in a simple manner by methods known to the person skilled in the art from a compound in which Q corresponds to the appropriate acid group —COOH by treating with thionyl chloride or with oxalyl chloride.

This reaction is carried out under suitable conditions in an inert solvent such as, for example, dichloromethane or 1,2-dichloroethane. For this purpose, the reaction mixture is heated with stirring. Preferably, the reaction is carried out under reflux conditions, whereby the temperature is set at the boiling temperature of the solvent employed.

Compounds of the formulae III and IV, which are needed as intermediates for the preparation of compounds of the formula I according to the invention, can be prepared, if they are not commercially available, by methods known to the person skilled in the art for corresponding compounds or by modified methods. Preparation methods are described, for example, in EP-A1-0 481 676 or J. Heterocycl. Chem. (1975) 12, 351 and ibid (1988) 25, 857. Corresponding compounds can be prepared as is described in the following examples or in an analogous manner.

Compounds of the formula I can also be prepared by subjecting compounds of the formula V

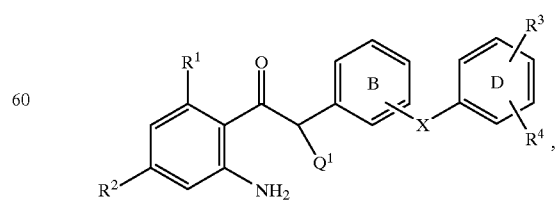

(V)

in which $R^1$, $R^2$, $R^3$ and $R^4$ and X have the given meanings, and $Q^1$ is a reactive carboxylate group which can have the meanings given above, but preferably an alkyl ester group having 1–4 C atoms in the alkyl such as, for example, methoxycarbonyl or ethoxycarbonyl, to a cyclization reaction and optionally converting by means of a subsequent hydrolysis into the desired compound of the formula I.

A compound V obtained as an intermediate, in which $Q^1$ is an alkyl ester group, can be obtained from the compounds of the formulae III and IV, in which the two substituents G and Q are each alkyl ester groups having 1–4 C atoms in the alkyl, by Claisen ester condensation. The reaction is carried out in the presence of a strong base, such as, for example, potassium hexamethyldisilazide, at elevated temperature. It is preferably carried out under reflux conditions such that the temperature is set approximately to the boiling temperature of the solvent.

The cyclization of a compound of the formula V to a compound of the formula I can be carried out under conditions which are known per se to the person skilled in the art or under slightly varied conditions. Preferably, this reaction is carried out in the presence of an acid. The cyclization reaction can be carried out directly, without isolating the previously prepared compound, in the same reaction solution.

Compounds of the formula I can furthermore be prepared from compounds of the formula VI

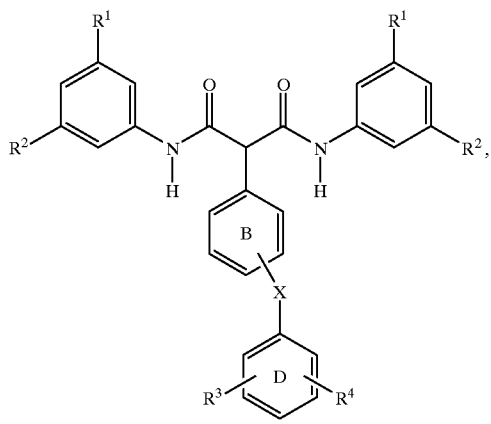

(VI)

in which $R^1$ to $R^4$ and X have the abovementioned meanings. The compounds of the formula VI can be prepared by reacting malonic acid derivatives of the formula VII

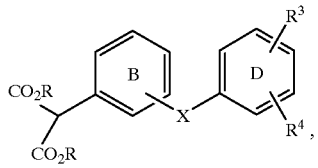

(VII)

in which $R^3$, $R^4$ and X have the meaning given above and R is an alkyl having 1–6 C atoms, with suitable compounds of the formula VIII

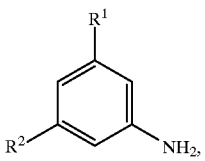

(VIII)

in which $R^1$ and $R^2$ have the meanings give above, under suitable conditions. Conditions such as are described in J. Heterocycl. Chem. (1988), 25, 857 are particularly suitable. The reaction conditions can easily be varied depending on the substituents. Preferably, the compounds of the formulae VII and VIII are heated together in a suitable solvent for approximately 15 to 20 hours. The reaction is preferably carried out under reflux conditions, the reaction temperature consequently being set to the boiling temperature of the solvent used.

The cyclization of compounds of the formula VI to compounds of the formula I can be carried out, as described in J. Heterocycl. Chem. (1988), 25, 857, in the presence of phosphorus pentoxide in methanesulfonic acid as a solvent.

The compounds of the formulae III, IV, IIV [sic] and VIII, and the precursors used therefor, if they are not commercially available, can be prepared by methods such as are described in the following examples or by modified methods such as are known to the person skilled in the art.

Furthermore, compounds of the formula I which have been prepared by one of the processes described above can be converted, if this is necessary, into other compounds of the formula I by methods known per se. In particular, it is often necessary following the cyclization reaction to remove protective groups previously introduced using suitable methods.

If the preparation of the compounds of the formula I leads to a stereoisomer mixture, the corresponding isomers can be separated by customary methods known to the person skilled in the art. Preferably, the separation of the isomers [sic] compounds can be carried out chromatographically. The compounds can be formed as a racemate mixture, as already indicated above, specifically synthesized as the individual enantiomer, or subsequently resolved into the pure enantiomers by utilizing differing solubilities of the salts in specific solvents. By methods known to the person skilled in the art, for this purpose, starting from the enantiomers according to the invention and suitable optically active acids, the corresponding salts are prepared, which can be resolved by fractional crystallization. Preferably, for this purpose optically active natural substances or their derivatives are used. Appropriate optically active acids are, for example (−)-di-p-tolyl-(D)-tartaric acid and/or (+)-D-p-tolyl-(D)-tartaric acid. The desired bases can then be liberated again by simple measures. The formation of diastereomeric esters or amides which can be separated chromatographically is also suitable for enantiomer resolution. After resolution has been carried out, the isomerically pure compounds can be liberated again.

The compounds of the general formula I and their physiologically acceptable salts can therefore be used for the production of pharmaceutical preparations by bringing them into the suitable dose form together with at least one excipient or auxiliary and, if desired, with one or more other active compounds. The preparations thus obtained can be employed as pharmaceuticals in human or veterinary medicine. Possible excipients are organic or inorganic substances which are suitable for enteral (e.g. oral or rectal) or parenteral administration and do not react with the novel compounds, for example water, vegetable oils, benzyl alcohols, polyethylene glycols, glycerol triacetate and other fatty acid glycerides, gelatine, soya lecithin, carbohydrates such as lactose or starch, magnesium stearate, talc or cellulose.

Tablets, coated tablets, capsules, syrups, juices or drops are used in particular for oral administration. Especially of interest are lacquered tablets and capsules having enteric coatings or capsule shells. Suppositories are used for rectal administration and solutions, preferably oily or aqueous solutions, furthermore suspensions, emulsions or implants, are used for parenteral administration.

The active compounds claimed according to the invention can also be lyophilized and the lyophilizates obtained used, for example, for the production of injection preparations or of infusion solutions.

The preparations indicated can be sterilized and/or can contain auxiliaries, such as preservatives, stabilizers and/or wetting agents, emulsifiers, salts for affecting the osmotic pressure, buffer substances, colourants and/or flavourings. If desired, they can also contain one or more further active compounds, e.g. one or more vitamins, diuretics or antiinflammatories.

Infusion solutions which contain one or more compounds of the formula I and/or their physiologically tolerable salts are prepared by generally customary methods. However, it is also possible to add one or more of the compounds according to the invention as active substances to a suitable, commercially available infusion solution shortly before use.

The compounds of formula I according to the invention are generally administered analogously to other known commercially available preparations for the indications claimed, preferably in doses between 0.1 mg and 500 mg, in particular between 5 and 300 mg per dose unit. The daily dose is preferably between approximately 0.01 and 250 mg/kg, in particular between 0.02 and 100 mg/kg of body weight.

The specific dose for each individual patient depends, however, on all sorts of factors, for example on the activity of the specific compound employed, on the age, body weight, general state of health, sex, on the diet, on the time and route of administration, on the excretion rate, pharmaceutical substance combination and severity of the particular disorder to which the therapy applies. Administration in the form of injection or infusion solutions is preferred.

In the following, examples are given which are used to illustrate the invention, but do not limit the invention to the examples given.

In the examples below, "customary working up" means: adding water, if necessary, extracting with dichloromethane, separating off, drying the organic phase over sodium sulfate, filtering, evaporating and purifying by chromatography on silica gel and/or by crystallization. Temperatures are given in ° C.

EXAMPLE 1

7-Chloro-1,2-dihydro-4-hydroxy-3-[3-((R,S)-1,2,3, 4-tetrahydro-2-methyl-4-isoquinolyl)phenyl] quinolin-2-one Starting substances (a) 2.7 g of methyl 3-(2-bromoacetyl)phenylacetate [obtainable by free-radical bromination of methyl 3-acetylphenylacetate] are dissolved in 30 ml of acetonitrile and added dropwise with stirring to a solution consisting of 2.8 g of N-methylbenzylamine and 20 ml of acetonitrile. The mixture is stirred at room temperature for 2 hours. The solvent is distilled off and the residue is treated with ether. This solution is worked up as is customary and 3-methoxycarbonylmethyl-alpha-benzylmethylaminoacetophenone is obtained.

aa) Analogously, but using dichloromethane as solvent, starting from ethyl 4-(2-bromoacetyl)phenylacetate and N-methylbenzylamine 4-ethoxycarbonylmethyl-alpha-benzylmethylaminoacetophenone is obtained.

b) 2-Benzylmethylamino-1-(3-methoxycarbonylmethylphenyl)ethanol 3.2 g of 3-methoxycarbonylmethyl-alpha-benzylmethylaminoacetophenone are dissolved in 15 ml of methanol. 0.39 g of NaBH$_4$ is added to the reaction mixture with stirring and cooling. The reaction solution is stirred for approximately one hour. The solvent is then removed, the residue is taken up with ether, and extracted three times by shaking with water. The organic phase is dried and the ether is distilled off. 2-Benzylmethylamino-1-(3-methoxycarbonylmethyl-phenyl)ethanol is obtained.

bb) Analogously, starting from 4-ethoxycarbonylmethyl-alpha-benzylmethylaminoacetophenone 2-benzylmethylamino-1-(4-ethoxycarbonylmethylphenyl)ethanol is obtained.

c) Methyl 3-[2-methyl-1,2,3,4-tetrahydro-4-(R,S)-isoquinolinyl]phenylacetate 1.5 g (4.8 mmol) of 2-benzylmethylamino-1-(3-methoxycarbonylmethylphenyl)ethanol are dissolved in 13 ml of dichloromethane. 3.7 ml of conc. sulfuric acid are added dropwise to this solution with cooling and stirring. It is stirred at room temperature for three hours. The reaction solution is diluted with dichloromethane and treated with ice. This solution is then adjusted to an alkaline pH using NaOH solution. The deposited organic phase is separated off. The aqueous phase is extracted twice more with dichloromethane. The combined organic phases are dried and the solvent is distilled off. The residue is taken up in ether and the solution is filtered. Methyl 3-[2-methyl-1,2,3,4-tetrahydro-4-(R,S)-isoquinolinyl]phenyl-acetate is obtained as an oil.

cc) Analogously, starting from 2-benzylmethylamino-1-(4-ethoxycarbonylmethylphenyl)ethanol ethyl 4-[2-methyl-1,2,3,4-tetrahydro-4-(R,S)-isoquinolinyl]phenylacetate is obtained, and from this the HCL salt by dissolving ethyl 4-[2-methyl-1,2,3,4-tetrahydro-4-(R,S)-isoquinolin-yl] phenylacetate in ether and treating with hydrochloric acid.

d) 3-[2-Methyl-1,2,3,4-tetrahydro-4-(R,S)-isoquinolinyl] phenylacetic acid 3.6 g of the ester obtained in the preceding reaction are treated with 36 ml of concentrated hydrochloric acid with cooling and stirring. The mixture is then boiled for 3 hours. The reaction solution is cooled, diluted with water and filtered. After customary working up, the acid is obtained.

dd) Analogously, starting from ethyl 4-[2-methyl-1,2,3,4-tetrahydro-4-(R,S)-isoquinolinyl]phenylacetate 4-[2-methyl-1,2,3,4-tetrahydro-4-(R,S)-isoquinolinyl] phenylacetic acid x HCl, m.p., 275–280° is obtained.

e) 3-[2-Methyl-1,2,3,4-tetrahydro-4-(R,S)-isoquinolinyl] phenylacetyl chloride 3.4 g (10.7 mmol) of 3-[2-methyl-1,2,3,4-tetrahydro-4-(R,S)-isoquinolinyl]phenylacetic acid are treated with 17.6 ml of thionyl chloride with stirring. The mixture is refluxed for one hour. The mixture is then evaporated to dryness. 3-[2-Methyl-1,2,3,4-tetrahydro-4-(R,S)-isoquinolinyl] phenylacetyl chloride is obtained.

ee) Analogously, starting from
4-[2-methyl-1,2,3,4-tetrahydro-4-(R,S)-isoquinolinyl] phenylacetic acid
4-[2-methyl-1,2,3,4-tetrahydro-4-(R,S)-isoquinolinyl] phenylacetyl chloride
is obtained.

f) Methyl 2-{3-[2-methyl-1,2,3,4-tetrahydro-4-(R,S)-isoquinolinyl]phenyl}acetamido-4-chlorobenzoate 2 g (10.7 mmol) of methyl 2-amino-4-chlorobenzoate are dissolved in 30 ml of dichloroethane and, after addition of 4.0 g of 3-[2-methyl-1,2,3,4-tetrahydro-4-(R,S)-isoquinolinyl]phenylacetyl chloride, dissolved in approximately 20 ml of dichloroethane, the mixture is heated under reflux for three hours. The solvent is then distilled off and the residue worked up as is customary. The residue is purified by chromatography on silica gel/dichloromethane (treated with 1–2% of methanol). Methyl 2-{3-[2-methyl-1,2,3,4-tetrahydro-4-(R,S)-isoquinolinyl]phenyl}acetami-do-4-chlorobenzoate is obtained.

ff) Analogously, starting from
4-[2-methyl-1,2,3,4-tetrahydro-4-(R,S)-isoquinolinyl] phenylacetyl chloride and methyl 2-amino-4-chlorobenzoate methyl 2-{4-[2-methyl-1,2,3,4-tetrahydro-4-(R,S)-isoquinolinyl]phenyl}acetamido-4-chlorobenzoate is obtained.

g) Methyl 2-{3-[2-methyl-1,2,3,4-tetrahydro-4-(R,S)-isoquinolinyl]phenyl}acetamido-4-chlorobenzoate Resolution of enantiomers:

500 mg of methyl 2-{3-[2-methyl-1,2,3,4-tetrahydro-4-(R,S)-isoquinolinyl]phenyl}acetamido-4-chlorobenzoate from the preceding reaction are added to a column (25×5 cm×cm [sic]), packed with a support for the resolution of enantiomers (Chiracel-OD) based on a cellulose derivative, and are resolved using an eluent consisting of hexane and i-propanol in the ratio 9:1, a flow rate of 40 ml/min being set (detection: UV 220 nm). Fractions which already contain the two enantiomers in high purities are chromatographed again.

Purity of enantiomers:
methyl (−)-2-{3-[2-methyl-1,2,3,4-tetrahydro-4-(R,S)-isoquinolinyl]phenyl}acetamido-4-chlorobenzoate ~100% ee
methyl (+)-2-{3-[2-methyl-1,2,3,4-tetrahydro-4-(R,S)-isoquinolinyl]phenyl}acetamido-4-chlorobenzoate ~98% ee h) 7-Chloro-1,2-dihydro-4-hydroxy-3-[3-((R,S)-1,2,3,4-tetrahydro-2-methyl-4-isoquinolyl)phenyl]-quinolin-2-one hydrate 1.2 g (2.7 mmol) of methyl 2-{3-[2-methyl-1,2,3,4-tetrahydro-4-(R,S)-isoquinolinyl]phenyl}acetamido-4-chlorobenzoate are dissolved in dried THF and cooled to approximately 5° C. 6 ml of a 1 molar $KN[Si(CH_3)_3]_2$ solution in THF are added dropwise at constant temperature with stirring under argon as protective gas. The mixture is stirred for a further hour. The reaction mixture is then treated with water and extracted with ether. The aqueous, alkaline phase is then acidified with 25% HCl, a viscous precipitate being formed. This precipitate is triturated with water, filtered off with suction, washed with further water and dried. The product mixture obtained is separated by chromatography on a silica gel column using a solvent mixture consisting of 70–80% THF and 20–30% methanol as eluent. 7-Chloro-1,2-dihydro-4-hydroxy-3-[3-((R,S)-1,2,3,4-tetrahydro-2-methyl-4-isoquinolyl)phenyl]quinolin-2-one hydrate (amorphous) is obtained.

Analogously, starting from
methyl 2-{4-[2-methyl-1,2,3,4-tetrahydro-4-(R,S)-isoquinolinyl]phenyl}acetamido-4-chlorobenzoate
7-chloro-1,2-dihydro-4-hydroxy-3-[4-((R,S)-1,2,3,4-tetrahydro-2-methyl-4-isoquinoline)phenyl]-quinolin-2-one [sic] is obtained. The crystalline HCl-containing product is obtained from this product if the product dissolved in water is precipitated by addition of hydrochloric acid.

i) 7-Chloro-1,2-dihydro-4-hydroxy-3-[3-((R,S)-1,2,3,4-tetrahydro-2-methyl-4-isoquinolyl)phenyl]-quinolin-2-one methanesulfonate 40 mg of 7-chloro-1,2-dihydro-4-hydroxy-3-[3-((R,S)-1,2,3,4-tetrahydro-2-methyl-4-isoquinolyl)phenyl]quinolin-2-one are briefly boiled together with 1 ml of ethanol and 0.02 ml of methanesulfonic acid. This reaction mixture is highly diluted with ether, the product depositing as a precipitate. The precipitate is separated off, washed with further ether and dried. 7-Chloro-1,2-dihydro-4-hydroxy-3-[3-((R,S)-1,2, 3,4-tetrahydro-2-methyl-4-isoquinolyl)-phenyl]quinolin-2-one methanesulfonate, amorphous, is obtained.

Analogously:
7-chloro-1,2-dihydro-4-hydroxy-3-[4-((R,S)-1,2,3,4-tetrahydro-2-methyl-4-isoquinolyl)phenyl]-quinolin-2-one methanesulfonate
5,7-dichloro-1,2-dihydro-4-hydroxy-3-[3-((R,S)-1,2,3,4-tetrahydro-2-methyl-4-isoquinolyl)phenyl]-quinolin-2-one
5,7-dichloro-1,2-dihydro-4-hydroxy-3-[4-((R,S)-1,2,3,4-tetrahydro-2-methyl-4-isoquinolyl)phenyl]-quinolin-2-one
7-chloro-1,2-dihydro-4-hydroxy-3-((R,S)-2-methyl-1,2,3,4-tetrahydro-4-phenylisoquinolin-6-yl)-quinolin-2-one
5,7-dichloro-1,2-dihydro-4-hydroxy-3-(((R,S)-2-methyl-1,2,3,4-tetrahydro-4-phenylisoquinolin-6-yl)quinolin-2-one
7-chloro-1,2-dihydro-4-hydroxy-3-((R,S)-2-methyl-1,2,3,4-tetrahydro-4-phenylisoquinolin-8-yl)-quinolin-2-one
5,7-dichloro-1,2-dihydro-4-hydroxy-3-((R,S)-2-methyl-1, 2,3, 4-tetrahydro-4-phenylisoquinolin-8-yl) -quinolin-2-one are obtained.

j) (−)-7-Chloro-1,2-dihydro-4-hydroxy-3-[3-((R,S)-1,2,3,4-tetrahydro-2-methyl-4-isoquinolyl)phenyl]-quinolin-2-one methanesulfonate 67.7 mg of methyl (−)-2-{3-[2-methyl-1,2,3,4-tetrahydro-4-(R,S)-isoquinolinyl]phenyl}acetamido-4-chlorobenzoate are dissolved in 3 ml of THF. 0.3 ml of a 1 molar solution, consisting of $KN[Si(CH_3)_3]_2$ and THF, are added dropwise with stirring under an argon atmosphere at a temperature of <10° C. The product formed by the reaction precipitates in crystalline form. The reaction solution is allowed to stand for approximately 12 hours. The solvent is then distilled off. The residue is dissolved in water. The aqueous solution is extracted with ether, acidified with hydrochloric acid and the aqueous solution is distilled off in a vacuum rotary evaporator. The residue is boiled with 2 ml of dried ethanol and 0.03 ml of methanesulfonic acid. The reaction mixture is treated with ether, the product depositing. (−)-7-Chloro-1, 2-dihydro-4-hydroxy-3-[3-((R,S)-1,2,3,4-tetrahydro-2-methyl-4-isoquinolyl]phenyl]quinolin-2-one methanesulfonate, amorphous, $[\alpha]_D^{20}=-7.60°$, is obtained.

k) (+)-7-Chloro-1,2-dihydro-4-hydroxy-3-[3-((R,S)-1,2,3,4-tetrahydro-2-methyl-4-isoquinolyl]phenyl-quinolin-2-one methanesulfonate 32 mg of methyl (+)-2-{3-[2-methyl-1,2,3,4-tetrahydro-4-(R,S)-isoquinolinyl]phenyl}acetamido-4-chlorobenzoate are dissolved in 2.5 ml of THF. 0.14 ml of a 1 molar solution of KN[Si(CH$_3$)$_3$]$_2$ in THF is added dropwise with stirring at a temperature of <10° C. The product formed by the reaction deposits in crystalline form. The reaction solution is allowed to stand for approximately 12 hours. The aqueous solution is then concentrated and the residue is dissolved in water. The aqueous solution is extracted with ether, acidified with hydrochloric acid and the solvent is distilled off in a vacuum rotary evaporator. The residue is briefly boiled with 2 ml of dried ethanol and 0.02 ml of methanesulfonic acid. The reaction mixture is treated with plenty of ether, the product depositing. (+)-7-Chloro-1,2-dihydro-4-hydroxy-3-[3-((R,S)-1,2,3,4-tetrahydro-2-methyl-4-isoquinolyl)phenyl]quinolin-2-one methanesulfonate, $[\alpha]_D^{20}$=+11° is obtained.

EXAMPLE 2

7-Chloro-3-[3-(2-dimethylaminomethylphenoxy)phenyl]-1,2-dihydro-4-hydroxyquinolin-2-one a) Ethyl 3-(2-cyanophenoxy)phenylacetate 4.23 g (35 mmol) of 2-fluorobenzonitrile, 6.3 g (35 mmol) of ethyl 3-hydroxyphenylacetate and 4.84 g of potassium carbonate (anhydrous) are dissolved in 40 ml of dimethylformamide and heated with stirring to a temperature of 160° C. Ethyl 3-(2-cyanophenoxy)-phenylacetate is formed takes place [sic]. The mixture is stirred for three hours while maintaining the temperature. The cooled reaction solution is treated with 150 ml of water and extracted with methyl t-butyl ether. The organic phase is separated off, washed with water and NaCl solution and dried. After distilling off the solvent, the product is obtained as an oil.

b) Ethyl 3-(2-aminomethylphenoxy)phenylacetate 8 g of the ethyl 3-(2-cyanophenoxy)phenylacetate obtained are dissolved in 200 ml of methanol and hydrogenated in the presence of 3.5 g of a Pd-C 5% catalyst. After the reaction has ended, the catalyst is filtered off. After customary working up, ethyl 3-(2-aminomethylphenoxy)-phenylacetate is obtained as an oil.

c) Ethyl 3-(2-dimethylaminomethylphenoxy)phenylacetate 7.3 g of the ethyl 3-(2-aminomethylphenoxy)phenylacetate (25 mmol) obtained as a residue is [sic] dissolved in 5.7 ml of 95% (150 mmol) formic acid [sic]. This reaction solution is heated to 80°. 5.6 ml of 37% formaldehyde solution are added dropwise with stirring in the course of half an hour and the mixture is stirred at reflux temperature for approximately 12 hours. The solvent is distilled off. The residue is adjusted to a basic pH using a bicarbonate solution, then extracted with methyl t-butyl ether. The organic phase is then washed with water and with an NaCl solution and dried. The ether is distilled off. The product is obtained as an oil. This is separated by chromatography using a solvent mixture consisting of methyl t-butyl ether and methanol (5%), in which 0.3% NH$_4$OH is dissolved, as eluent.

d) 3-(2-Dimethylaminomethylphenoxy)phenylacetic acid

The ethyl 3-(2-dimethylaminomethylphenoxy)phenylacetate acid obtained by the preceding reaction is dissolved in 20 ml of 25% hydrochloric acid and heated under reflux with stirring for five hours. The solvent is then distilled off. The residue is taken up in toluene. The solvent is distilled off again to a residue. The residue is triturated with acetone, the product being obtained in crystalline form. The crystals are filtered off with suction, washed with acetone and air-dried. 3-(2-Dimethylaminomethylphenoxy)-phenylacetic acid, m.p. 205–208°, is obtained.

e) 3-(2-Dimethylaminomethylphenoxy)phenylacetyl chloride 2 g of 3-(2-dimethylaminomethylphenoxy)-phenylacetic acid are treated with 20 ml of thionyl chloride and heated with stirring and under reflux for ½ an hour. The solvent is then removed. The residue is taken up with toluene and the solvent is again distilled off.

f) Methyl 2-[3-(2-dimethylaminomethylphenoxy)phenyl)-acetamido]-4-chlorobenzoate 3-(2-Dimethylaminomethylphenoxy)phenylacetyl-chloride is dissolved in 30 ml of -dichloromethane and, after addition of 1.1 g of methyl 2-amino-4-chlorobenzoate, boiled for a period of one hour. The solvent is distilled off. The residue obtained is taken up in dichloromethane, and the mixture is washed with sodium carbonate solution, water and then with an NaCl solution. The organic phase is separated off, the solvent is distilled off and the residue is separated by chromatography using methyl t-butyl ether/methanol (5%)/NH$_4$OH (0–0.3%) as eluent.

g) 7-Chloro-3-[3-(2-dimethylaminomethylphenoxy)-phenyl]-1,2-dihydro-4-hydroxyquinolin-2-one 1.2 g of methyl 2-[3-(2-dimethylaminomethyl-phenoxy)phenyl) acetamido]-4-chlorobenzoate are dissolved in 45 ml of dried THF. 5.5 ml of a 1 molar KN[Si(CH$_3$)$_3$]$_2$ solution in THF are then added with stirring at a temperature below 10°. The mixture is additionally stirred at room temperature for approximately 12 hours, a precipitate being formed. After customary working up, 7-chloro-3-[3-(2-dimethylamino-methylphenoxy)phenyl]-1,2-dihydro-4-hydroxyquinolin-2-one (crude product) is obtained.

Analogously, as described in Example 1, starting from a sample of the 7-chloro-3-[3-(2-dimethyl-aminomethylphenoxy)phenyl]-1,2-dihydro-4-hydroxyquinolin-2-one prepared, the corresponding methanesulfonate is prepared.

Analogously, 5,7-dichloro-3-[3-(2-dimethylaminomethylphenoxy)-phenyl]-1,2-dihydro-4-hydroxyquinolin-2-one 7-chloro-3-[3-(3-dimethylaminoethylphenoxy)phenyl]-1,2-dihydro-4-hydroxyquinolin-2-one 5,7-dichloro-3-[3-(3-dimethylaminomethylphenoxy)-phenyl]-1,2-dihydro-4-hydroxyquinolin-2-one 7-chloro-3-[3-(4-dimethylaminomethylphenoxy)-phenyl]-1,2-dihydro-4-hydroxyquinolin-2-one 5,7-3-[3-(4-dimethylaminomethylphenoxy)phenyl]-1,2-dihydro-4-hydroxyquinolin-2-one are obtained.

EXAMPLE 3

7-Chloro-3-[3-(dimethylaminophenylmethyl)phenyl]-1,2-dihydro-4-hydroxyquinolin-2-one a) 3-(Hydroxyphenylmethyl)phenylacetonitrile 3-(Hydroxyphenylmethyl)phenylacetonitrile is prepared from commercially available 3-methyl-benzophenone, as described in Eur. J. M. C. 9, 381 (1974).

b) 3-(Chlorophenylmethyl)phenylacetonitrile 9 g of 3-hydroxyphenylmethyl)phenylacetonitrile are dissolved in 150 ml of toluene and treated with stirring with 5.8 ml (80 mmol) of thionyl chloride. The reaction mixture is heated to reflux temperature and stirred for one hour. In the course of this, approximately 50 ml of toluene are removed in a water separator. The solvent is removed and 3-(chlorophenyl-methyl)phenylacetonitrile is obtained.

c) 3-(Dimethylaminophenylmethyl)phenylacetonitrile

Without further working up, the residue obtained in the preceding reaction is treated with 80 ml of a 20% dimethylamine solution in methanol. The reaction solution is allowed to stand at room temperature for approximately 12 hours. The solvent is distilled off and the residue is taken up in ether. The ether phase is washed with water and then with 2 N HCl. The ether phase is discarded and the hydrochloric acid-containing aqueous phase is rendered alkaline using concentrated NaOH solution. It is extracted with ether and the ether phase is filtered after drying. The ether is distilled off. 3-(Dimethylaminophenylmethyl)-phenylacetonitrile is obtained as an oil.

d) 3-(Dimethylaminophenylmethyl)phenylacetic acid 3.3 g of 3-(dimethylaminophenylmethyl)phenyl-acetonitrile are taken up in a mixture consisting of 25 ml of concentrated sulfuric acid, 25 ml of glacial acetic acid and 25 ml of water and boiled with stirring for 20 hours. The solvent mixture is distilled off and the residue is dissolved in water. The solution is then treated with sufficient $BaCl_2$ solution (about 80 g of $BaCl_2$) until the filtrate of the precipitate filtered off with suction through kieselguhr no longer gives a $BaSO_4$ precipitate. The filtrate is distilled off to a residue. The residue is suspended in ethanol and the insoluble components are filtered off. The filtrate is again distilled off to a residue, treated with water and rendered alkaline with concentrated ammonia solution. This solution is extracted with dichloromethane and the dichloromethane phase is dried. After customary working up, the ethyl ester is obtained in the form of an oil. 1.7 g of this oil are boiled for 3 hours in 20 ml of 25% hydrochloric acid. The solution is then concentrated to dryness. 3-(Dimethylaminophenylmethyl)-phenylacetic acid (amorphous) is obtained.

e) 3-(Dimethylaminophenylmethyl)phenylacetyl chloride 1.5 g of 3-(dimethylaminophenylmethyl)phenylacetic acid are heated at reflux temperature for ½ an hour in 15 ml of thionyl chloride with stirring. Thionyl chloride not consumed in the reaction is distilled off. The residue is taken up in toluene and the solvent is distilled again.

f) Methyl 3-(dimethylaminophenylmethyl)phenyl-2-acetamido-4-chlorobenzoate 3-(Dimethylaminophenylmethyl)phenylacetyl chloride is dissolved in 30 ml of dichloroethane. 0.9 g (5 mmol) of methyl 2-amino-4-chlorobenzoate is added and the mixture is heated under reflux for approximately ½ an hour. The solvent is then distilled off. The residue is taken up in dichloromethane and washed with water, sodium carbonate solution and NaCl solution. The organic phase is dried, the solvent is distilled off and the residual oil is separated by chromatography on a column packed with silica gel using an eluent consisting of dichloromethane, 1–2% methanol and 0.1–0.2% $NH_4OH$. Methyl 3-(dimethylaminophenylmethyl)phenyl-2-acetamido-4-chlorobenzoate is obtained as an oil.

g) 7-Chloro-3-[dimethylaminophenylmethyl)phenyl]-1,2-dihydro-4-hydroxyquinolin-2-one 2.0 g (4.6 mmol) of methyl 3-(dimethylaminophenylmethyl)phenyl-2-acetamido-4-chlorobenzoate are dissolved in 15 ml of THF. With cooling, 15 ml of a 1 molar solution of THF and $KN[Si(CH_3)_3]_2$ are added dropwise with stirring. The mixture is additionally stirred at room temperature for 1 ½ hours. The solvent is distilled off and the residue is treated with water. The solution thus obtained is washed with dichloromethane. The aqueous phase is adjusted to an acidic pH using hydrochloric acid and again extracted with dichloromethane. The organic phase separated off is dried. The solvent is distilled off. For further purification of the oil obtained, the product is taken up with ethanol, acidified with ethereal hydrochloric acid, triturated with ether and the product obtained is filtered off with suction. 7-Chloro-3-[dimethylamino-phenylmethyl)phenyl]-1,2-dihydro-4-hydroxyquinolin-2-one hydrochloride, dihydrate, m.p. ~230°, is obtained.

Analogously:

5,7-dichloro-3-[3-(dimethylaminophenylmethyl)-phenyl]-1,2-dihydro-4-hydroxyquinolin-2-one 7-chloro-3-[3-(methylaminophenylmethyl)phenyl]-1,2-dihydro-4-hydroxyquinolin-2-one 5,7-dichloro-3-[3-(methylaminophenylmethyl)phenyl]-1,2-dihydro-4-hydroxyquinolin-2-one 7-chloro-3-[3-(isopropylaminophenylmethyl)phenyl]-1,2-dihydro-4-hydroxyquinolin-2-one 5,7-dichloro-3-[[lacuna]-(isopropylaminophenyl-methyl)-phenyl]-1,2-dihydro-4-hydroxyquinolin-2-one are obtained.

EXAMPLE 4

7-Chloro-3-[4-(2-dimethylaminomethylbenzyl)phenyl]-1,2-dihydro-4-hydroxyquinolin-2-one a) Ethyl 2-(4-formylphenyl)acetate 25.7 g of ethyl 4-bromomethylphenylacetate and 28 g of hexamethylenetetramine are dissolved in 200 ml of 20% acetic acid, heated to 100° C. with stirring and stirred for four hours. The reaction solution is allowed to cool and sufficient sodium carbonate is added until a saturated solution is obtained. This solution is extracted with ether, dried and the ether is then removed. The residue is purified by chromatography (silica gel/methyl t-butyl ether/ether 1:1).

b) Ethyl (2-(N,N-dimethylaminomethyl)phenyl)hydroxy-methyl-4-phenylacetate 3 ml of N,N-dimethylbenzylamine are dissolved in 20 ml of diethyl ether and 25 ml of a 6 molar n-butyllithium solution are added at room temperature with stirring. The mixture is additionally stirred at room temperature for 24 hours, a precipitate being formed. 3.84 g of ethyl 2-(4-formylphenyl)acetate dissolved in 20 ml of diethyl ether are added dropwise at 0° C. to the solution obtained and the mixture is then stirred for 4 hours at room temperature. It is then worked up as is customary. Ethyl (2-(N,N-dimethylamino-methyl)phenyl)hydroxymethyl-4-phenylacetate (oil) is obtained.

c) Ethyl (2-(N,N-dimethylaminomethyl)phenyl)methyl-4-phenylacetate 40 ml of trifluoroacetic acid are cooled to 0°. 2 g of $NaBH_4$ is [Sic] introduced in portions with stirring. At 15°, 3.8 g of ethyl (2-(N,N-dimethylaminomethyl)phenyl) hydroxymethyl-4-phenyl-acetate, dissolved in 30 ml of dichloromethane, are then added dropwise. The mixture is additionally stirred at room temperature for 24 hours, poured onto ice and adjusted to an alkaline pH using concentrated NaOH solution. The solution obtained is extracted with dichloromethane. The organic phase separated off is washed with an NaCl solution and dried. The solvent is then distilled off and the residue is dissolved in methyl tert-butyl ether and filtered. After removing the solvent, a yellow oil is obtained, which is purified by chromatography (silica gel/methyl tert-butyl ether:diethyl ether 1:1). Ethyl (2-(N,N-dimethylaminomethyl)-phenyl)methyl-4-phenylacetate is obtained.

d) (2-(N,N-Dimethylaminomethyl)phenyl)methyl-4-phenylacetic acid 600 mg of ethyl (2-(N,N-dimethylaminomethyl)-phenyl)methyl-4-phenylacetate are dissolved in 15 ml of 25% hydrochloric acid and heated under reflux for five hours. The mixture is evaporated to dryness. The residue is taken up in toluene and the solvent is distilled off again. (2-(N,N-Dimethylaminomethyl) phenyl)methyl-4-phenylacetic acid hydrochloride is obtained.

e) Methyl (2-N,N-dimethylaminomethylbenzyl)-4-phenyl-acetamido-2-(4-chlorobenzoate) 600 mg of (2-(N,N-dimethylaminomethyl)phenyl)-methyl-4-phenylacetic acid (hydrochloride) are heated under reflux with 10 ml of thionyl chloride for ½ an hour. This solution is concentrated and this is [sic] taken up in toluene. The toluene is distilled off again. The acid chloride thus obtained is taken up in 10 ml of dichloromethane, 353 mg of methyl 2-amino-4-chlorobenzoate are added and the mixture is heated under reflux for one hour. The solvent is distilled off. After customary working up, methyl (2-N,N-dimethylamino-methylbenzyl)-4-phenylacetamido-2-(4-chlorobenzoate) is obtained as an oil.

f) 7-Chloro-3-[4-(2-dimethylaminomethylbenzyl)-phenyl]-1,2-dihydro-4-hydroxyquinolin-2-one dimethanesulfonate 500 mg of methyl (2-N,N-dimethylaminomethyl-benzyl)-4-phenylacetamido-2-(4-chlorobenzoate) are dissolved in 20 ml of THF. 2.5 ml of a 1 molar KN[Si(CH$_3$)$_3$]$_2$ solution in THF are added with stirring at a temperature <10° C. The mixture is additionally stirred at room temperature for approximately 12 hours. A fine precipitate is formed, which goes into solution again by addition of methanol. The reaction solution is distilled off to a residue and this is dissolved in water. After customary working up, 7-chloro-3-[4-(2-dimethylaminomethylbenzyl)phenyl]-1, 2-dihydro-4-hydroxyquinolin-2-one dimethanesulfonate, m.p. 100°, is obtained.

Analogously:

5,7-dichloro-3-[4-(2-dimethylaminomethylbenzyl)-phenyl]-1,2-dihydro-4-hydroxyquinolin-2-one 7-chloro-3-[3-(2-dimethylaminomethylbenzyl)-phenyl]-1,2-dihydro-4-hydroxyquinolin-2-one 5,7-dichloro-3-[3-(2-dimethylaminomethylbenzyl)-5 phenyl]-1,2-dihydro-4-hydroxyquinolin-2-one 7-chloro-3-[3-(3-dimethylaminomethylbenzyl)-phenyl]-1,2-dihydro-4-hydroxyquinolin-2-one 5,7-dichloro-3-[3-(3-dimethylaminomethylbenzyl)-phenyl]-1,2-dihydro-4-hydroxyquinolin-2-one 7-chloro-3-[3-(4-dimethylaminomethylbenzyl)-phenyl]-1,2-dihydro-4-hydroxyquinolin-2-one 5,7-dichloro-3-[3-(4-dimethylaminomethylbenzyl)-phenyl]-1,2-dihydro-4-hydroxyquinolin-2-one 7-chloro-3-(4-dimethylaminomethyl-3-phenoxy-phenyl)-1,2-dihydro-4-hydroxyquinolin-2-one are obtained.

Examples of pharmaceutical formulations

Example A: Injection vials

A solution of 100 g of an active compound of the formula I and 5 g of disodium hydrogen phosphate are [sic] adjusted to pH 6.5 in 3 l of double-distilled water using 2 N hydrochloric acid, sterile filtered, dispensed into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into moulds and allowed to cool. Each suppository contains 20 mg of active compound.

Example C: Solution

A solution of 1 g of an active compound of the formula I, 9.38 g of NaH$_2$PO$_4$·2H$_2$O, 28.48 g of Na$_2$HPO$_4$·12H$_2$O and 0.1 g of benzalkonium chloride in 940 ml of double-distilled water is prepared. It is adjusted to pH 6.8, made up to 1 l and sterilized by irradiation.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated Tablets

Analogously to Example E, tablets are pressed which are then coated in a customary manner with a coating of sucrose, potato starch, talc, tragacanth and colorant.

Example G: Capsules 2 kg of active compound of the formula I are filled in a customary manner into hard gelatine capsules such that each capsule contains 20 mg of the active compound.

Example H: Ampoules

A solution of 1 kg of active compound of the formula I in 60 l of double-distilled water is sterile filtered, dispensed into ampoules, lyophilized under sterile conditions and aseptically sealed. Each ampoule contains 10 mg of active compound.

We claim:

1. A quinolin-2-(1H)-one compound of the formula I

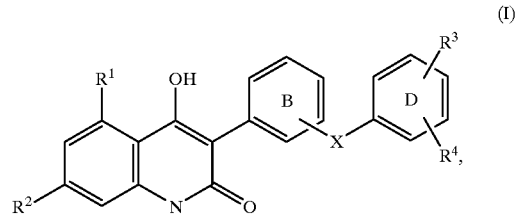

in which

R$^1$, R$^2$ and R$^3$ are in each case independently of one another H, Hal, A or OA, R$^4$ is H, —(CH$_2$)$_m$—NR$^6$R$^7$, R$^5$ is H, —(CH$_2$)$_n$—NR$^6$R$^7$, R$^6$ is H, A or, together with R$^7$, —(CH$_2$)$_4$— or —(CH$_2$)$_5$—, R$^7$ is H, A or —(CH$_2$)$_m$— with a bond to the same ring or adjacent ring B or D or, together with R$^6$, —(CH$_2$)$_4$— or —(CH$_2$)$_5$—, X is —CHR$^5$—, —NR$^5$—, —O—, —S—, A is alkyl having 1–6 C atoms, Hal is F, Cl, Br or I, m is 1–3 and n is 0–3, where at least one of the two radicals R$^4$ or R$^5$ has the meaning —(CH$_2$)$_m$—NR$^6$R$^7$ or —(CH$_2$)$_n$—NR$^6$R$^7$ or an enantiomer, or a diastereomer, or a phisiologically aceptable or a solevent thereof.

2. A compound which is an enantiomer or diastereomer of the compound according to claim 1.

3. A pharmaceutical composition, comprising:

at least one compound of formula I according to claim 1, or one of its physiologically acceptable salts and a pharmaceutically acceptable excipient.

4. A process for the production of a pharmaceutical composition of claim 3, comprising:

bringing a compound of the formula I according to claim 1, one of its physiologically tolerable salts, enantiomers, or diastereomers into a dose form together with at least one solid, liquid or semiliquid excipient or auxiliary.

5. A medicament composition comprising at least one compound of the formula I according to claim 1 or a physiologically acceptable salt or an enantiomer or diastereomer thereof and a pharmaceutically acceptable excipient.

6. A quinolin-2-(1H)-one compound of claim 1 which is 7-chloro-1,2-dihydro-4-hydroxy-3-[3- R, S) -1,2,3,4-tetrahydro-2-methyl-4-isoquinolinyl) phenyl]quinolin-2-one or an enantiomer, a diastereomer, a physiologically acceptable salt or solvate thereof.

7. A process for the preparation of a quinolin-2-(1H)- one compound of the formula I of claim 1, comprising:

supplying a compound of the formula III

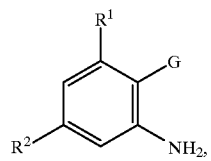
(III)

in which
R$^1$ and R$^2$ are in each case independently of one another,
H, Hal, A or OA, and
G is a cyano group or a reactive carboxylate group,
reacting the compound of the formula III with a compound of the formula IV

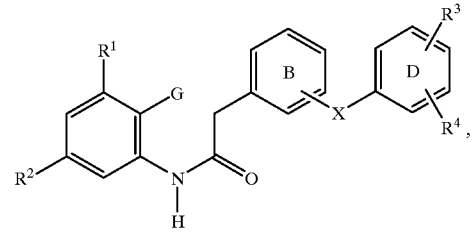
(IV)

in which
R$^3$ is H, Hal, A or OA,
R$^4$ is H, —(CH$_2$)$_m$—NR$^6$R$^7$,
X is —CHR$^5$—, —NR$^5$—, —O—, —S—, and
Hal, A, R$^5$, R$^6$, R$^7$, are as defined in claim 1
Q is a reactive carboxylate group,
to give a compound of the formula II (II)

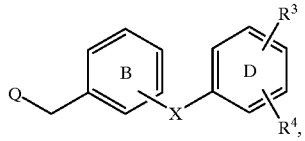

in which
R$^1$, R$^2$, R$^3$, R$^4$, X, and G are as defined above, and then
cyclizing the compound of the formula II in the presence of a base to give a compound of the formula I

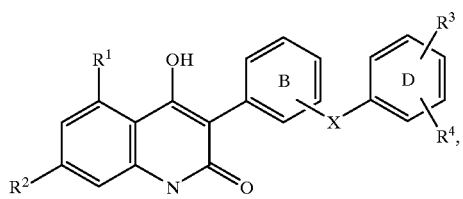
(I)

in which R$^1$, R$^2$, R$^3$, R$^4$, and X are as defined above.

8. A process for the preparation of a quinolin-2-(1H)- one compound of the formula I, of claim 1 comprising:

supplying a compound of the formula III

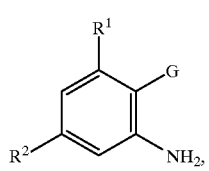
(III)

in which
R$^1$ and R$^2$ are in each case independently of one another, H, Hal, A or OA, and
G is an alkyl ester group having 1–4 C atoms in the alkyl,
reacting the compound of the formula III with a compound of the formula IV (IV)

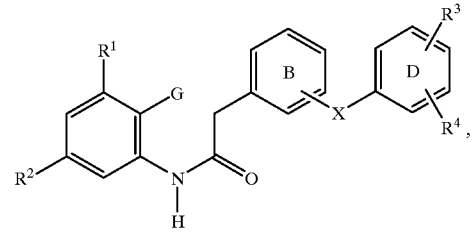

in which
R$^3$ is H, Hal, A or OA,
R$^4$ is H, —(CH$_2$)$_m$—NR$^6$R$^7$,
X is —CHR$^5$—, —NR$^5$—, —O—, —S—, and
Hal, A, R$^5$, R$^6$, R$^7$ are as defined in claim 1
Q is an alkyl ester group having 1–4 carbon atoms in the alkyl,
to give a compound of the formula V (V)

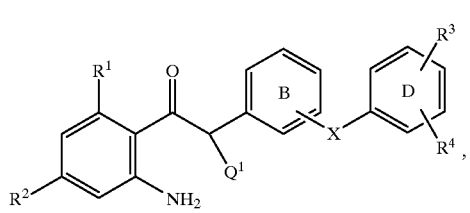

in which
R$^1$, R$^2$, R$^3$, R$^4$, and X are as defined above, and Q$^1$ is a reactive carboxylate group, then
cyclizing the compound of the formula V in the presence of an acid to give a compound of the formula I

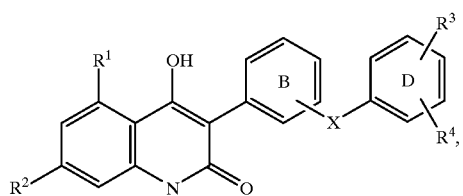
(I)

in which R$^1$, R$^2$, R$^3$, R$^4$, and X are as defined above.

9. A process for the preparation of a quinolin-2-(1H)- one compound of the formula I, of claim 1 comprising:
supplying a compound of the formula VII

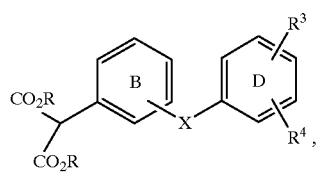
(VII)

in which
R$^3$ is H, Hal, A or OA,
R$^4$ is H, —(CH$_2$)$_m$—NR$^6$R$^7$,
X is —CHR$^5$—, —NR$^5$—, —O—, —S—, and
Hal, A, R$^5$, R$^6$, R$^7$ are as defined in claim 1
R is an alkyl having 1–6 carbon atoms,
reacting the compound of the formula VII with a compound of the formula VIII

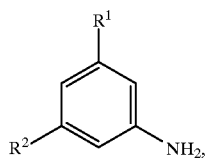
(VIII)

in which
R$^1$ and R$^2$ are in each case independently of one another, H, Hal, A or OA, to give a compound of the formula VI

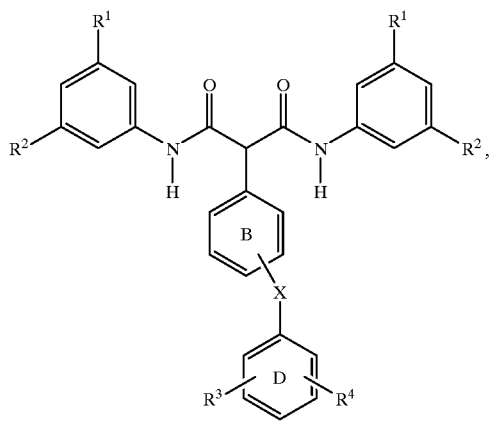
(VI)

in which
R$^1$, R$^2$, R$^3$, R$^4$, and X are as defined above
cyclizing the compound of the formula VI to give a compound of the formula I

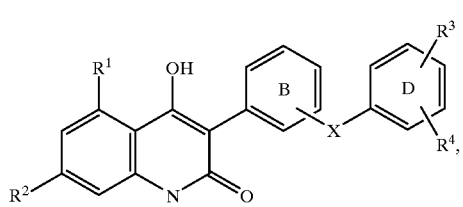
(I)

in which R$^1$, R$^2$, R$^3$, R$^4$, and X are as defined above.

10. A process as claimed in claim 7, wherein the base used for cyclizing the compound of the formula II is sodium hydride or potassium hexamethyldisilazide.

11. A method of antagonizing the NMDA receptor in a patient suffering from a central nervous system disorder comprising supplying a NMDA receptor antagonizing amount of a compound of the formula 1 according to claim 1, or the compound's physiologically acceptable salts, enantiomers, or diastereomers, to a patient in need thereof.

12. A process for the treatment of a disease caused by stroke or other cerebral trauma in a patient comprising supplying an effective amount of a compound of the formula 1 according to claim 1, or the compound's physiologically acceptable salts, enantiomers, or diastereomers, to a patient in need thereof.

13. A process for the treatment of disease medicated by NMDA receptor in a patient comprising supplying an effective amount of a compound of the formula 1 according to claim 1, or the compound's physiologically acceptable salts, enantiomers, or diastereomers, to a patient in need thereof.

14. A compound which is an enantiomer, stereoisomer, physiologically acceptable salt, or solvate of the compound of claim 6.

* * * * *